US00PP23289P2

(12) United States Plant Patent
Bédard

(10) Patent No.: US PP23,289 P2
(45) Date of Patent: Jan. 1, 2013

(54) FLORIBUNDA ROSE PLANT NAMED 'WEKZAZETTE'

(50) Latin Name: *Rosa hybrida*
Varietal Denomination: WEKzazette

(75) Inventor: Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 13/317,757

(22) Filed: Oct. 27, 2011

(51) Int. Cl.
*A01H 5/00* (2006.01)

(52) U.S. Cl. ..... Plt./142

(58) Field of Classification Search ..... Plt./142
See application file for complete search history.

*Primary Examiner* — June Hwu
*Assistant Examiner* — Louanne Krawczewicz Myers
(74) *Attorney, Agent, or Firm* — McKee, Voorhees & Sease, P.L.C.

(57) ABSTRACT

A new variety of Floribunda rose suitable for garden decoration, having flowers of ketchup red and mustard yellow bicolor coloration.

1 Drawing Sheet

Classification: The present invention relates to a new *Rosa hybrida* plant.

Variety denomination: The new plant has the varietal denomination 'WEKzazette'.

BACKGROUND OF THE INVENTION

This invention relates to a new and distinct variety of Floribunda Rose. It has as its seed parent the variety known as 'WEKsanpoly' (U.S. Plant Pat. No. 13,513) and as its pollen parent the variety known as 'WEKgojolo' (U.S. Plant Pat. No. 21,531).

SUMMARY OF THE INVENTION

Among the features which distinguish the new variety from other presently available and commercial rose cultivars known to the inventor are the following combinations of characteristics: its unusual ketchup red and mustard yellow bicolor flower coloration, its excellent color stability throughout the life of the flower, its dark yellow green style and its strong red suffusion on the inner surface of the sepal that appears as the flower ages. The plant has a bushy upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKzazette' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKsanpoly' by the following combination of characteristics: whereas 'WEKzazette' bears flowers of ketchup red and mustard yellow bicolor coloration, 'WEKsanpoly' bears flowers of even medium red coloration. The new variety has a bushy upright medium height growing habit (about 120 to about 160 cm. in height), whereas the seed parent has a rounded bushy to somewhat upright significantly shorter growing habit (about 88 to about 105 cm. in height).

The new variety may be distinguished from its pollen parent, 'WEKgojolo' by the following combination of characteristics: whereas 'WEKzazette' bears flowers of ketchup red and mustard yellow bicolor coloration, 'WEKgojolo' bears flowers of neon yellow coloration. 'WEKzazette' bears its flowers singly, whereas 'WEKgojolo' usually bears its flowers in clusters of three to five or more per stem. The new variety has a bushy upright medium height growing habit (about 120 to about 160 cm. in height), whereas the pollen parent has a bushy upright significantly shorter growing habit (about 90 to about 110 cm. in height).

COMPARISON WITH THE CLOSEST COMMERCIALLY AVAILABLE CULTIVAR

The new variety may be distinguished from its closest commercially available cultivar, 'WEKwinwin' (U.S. Plant Pat. No. 11,382) by the following combination of characteristics: whereas 'WEKzazette' bears double flowers (about 20 to 28 petals), 'WEKwinwin' bears double flowers with heavier petalage (about 26 to 30 petals). 'WEKzazette' has somewhat small foliage (about 6.7 to about 13.1 cm. in length and about 5.7 to about 9.5 cm. in width at the widest point), whereas 'WEKwinwin' has significantly larger and longer foliage (about 10.5 to about 15 cm. in length and about 8.5 to about 11.5 cm. in width at the widest point). The new variety has a bushy upright medium height growing habit (about 120 to about 160 cm. in height), whereas the closest commercially available cultivar has an upright to slightly spreading shorter growing habit (about 120 to about 140 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The following photograph illustrates a 3 to 4 year-old rose plant of the new variety grown outdoors in Pomona, Calif. the month of October. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety bears its flowers singly. Flowers are borne on strong short to medium length stems (about 13 to about 38 cm.). Outdoors, the plant blooms very abundantly and nearly continuously during the growing season. The flowers have a slight tea to apple-like fragrance.

BUD

The peduncle is about 3.9 to about 5.9 cm. in length, of average caliper (about 0.2 to about 0.3 cm. in diameter), and usually erect. It is somewhat rough, with some stipitate glands. Peduncle color is between 146C and 148B sometimes moderately suffused, especially on the side exposed to the sun, with between 183B and 187B.

Before the calyx breaks, the bud is about 1.2 to about 1.6 cm. in diameter at the widest point, about 1.3 to about 2.4 cm. in length, and pointed to somewhat ovoid in shape. The surface of the bud bears between 5 to 8 foliaceous appendages and some stipitate glands, usually with slender entire foliaceous parts extending beyond the tip of the bud about ¼ or more of its length. Bud color is between 146B and 146A sometimes moderately suffused, especially on the side exposed to the sun, with between 183B and 187A.

The sepals are about 2.6 to about 3.6 cm. in length and about 0.8 to about 1.2 cm. in width at the widest point. The outer surface color of the sepal is between 146B and 146A sometimes moderately suffused, especially on the side exposed to the sun, with between 183B and 187A. The outer surface texture of the sepal is smooth with some stipitate glands. The inner surface color of the sepal is near 146B broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with many stipitate glands.

The receptacle of the flower is of moderately short to medium length (about 0.4 to about 0.6 cm.) and average in caliper (about 0.6 to about 0.8 cm. in diameter). The receptacle is urn-shaped in form. Its surface is very smooth with somewhat thin fleshy walls. The receptacle color is between 144A and 146B.

As the petals open (after the calyx breaks), the bud is about 1.4 to about 1.9 cm. in diameter at the widest point, about 2.0 to about 2.9 cm. in length, and moderately ovoid to somewhat pointed in form. The color at the base of the under surfaces of the newly opened petals is between 6C and 4A gradually suffusing toward the middle of the petal with between 21D and 22C sometimes moderately suffused on the outermost petals with between 53A and 187C. There is no visible change in coloration at the point where the petal attaches. The color of the upper surfaces of the newly opened petals is between 53A and 46A. At the point where the petal attaches, there is a moderately large zone of between 3A and 5A.

BLOOM

When fully open, the bloom ranges from about 6.5 to about 10.7 cm. in diameter. Petalage is double with about 20 to 28 petals and about 1 to 13 petaloids irregularly arranged. When partially open, the bloom form is moderately high centered to somewhat ovoid, and the petals are somewhat tightly spiraled to cupped with petal edges moderately reflexed outward. When fully open, the bloom form is cupped, and the petals loosely cupped to moderately undulated with petal edges very reflexed to somewhat rolled outward.

PETALS

The substance of the petals is moderately heavy and of somewhat thin to medium thickness, with upper surfaces satiny to moderately velvety and under surfaces matte. The petals are about 2.6 to about 4.4 cm. in length and about 2.0 to about 4.2 cm. in width at the widest point. Petal margins are entire.

The outer petals are obovate in shape with rounded apices.

The inner petals are obovate to somewhat oblanceolate in shape with rounded apices and sometimes slightly notched with one to two notches.

Petaloids are about 1.1 to about 3.1 cm. in length and about 0.3 to about 2.1 cm. in width at the widest point. Petaloids are irregularly shaped somewhat oblanceolate to subulate with rounded apices.

NEWLY OPENED FLOWER

The color at the base of the under surfaces of the outer petals is between 6C and 7C gradually suffusing toward the middle of the petal with between 18A and 14C often moderately suffused with between 60B and 60A. There is no visible change in coloration at the point where the petal attaches. The upper surface color of the outer petals is between 46A and 45A sometimes lightly suffused on the outermost petals with between 187A and 187B. At the point where the petal attaches, there is a moderately large zone of between 6A and 9B.

The color at the base of the under surfaces of the intermediate and inner petals is between 6C and 7C gradually suffusing toward the middle of the petal with between 18A and 14C sometimes lightly suffused with between 60B and 60A. There is no visible change in coloration at the point where the petal attaches. The upper surface color of the intermediate and inner petals is between 45A and 46B.

The under and upper surface colors of the petaloids are similar in coloration to the upper and under surfaces of the intermediate and inner petals.

The general tonality of the newly opened flower is between 45A and 46B.

THREE-DAY-OLD FLOWER

The color at the base of the under surfaces of the outer, intermediate and inner petals is between 5D and 6D gradually suffusing toward the middle of the petal with between 18C and 19D sometimes moderately suffused with between 60B and 60C. The suffusion is more evident on the outermost petals. There is no visible change in coloration at the point where the petal attaches. The upper surface color of the outer, intermediate and inner petals is between 53C and 53B sometimes lightly suffused on the outermost petals with between 187A and 187B. At the point where the petal attaches, there is a moderately large zone of between 4B and 3C.

The under and upper surface colors of the petaloids are similar in coloration to the upper and under surfaces of the intermediate and inner petals.

The general tonality of the three-day-old flower is between 53C and 53B sometimes lightly suffused on the outermost petals with between 187A and 187B.

On the spent bloom, the petals usually drop off cleanly and are not particularly affected by cold, hot, wet, or dry weather.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 145) and are arranged regularly about the pistils; a few are mixed with petaloids. The filaments are of somewhat short to medium length (about 0.5 to about 1.2 cm.) most with anthers. Filaments are between 14A and 13A in color. The anthers are moderately small for the class and all open approximately at the same time. Anther color when immature is near 23B on the external part and near 13D on the internal part. Anther color at maturity is near 164C on the external part and near 200A on the internal part. Pollen is very abundant and between 16A and 21C in color.

FEMALE REPRODUCTIVE ORGANS

Pistils vary in number (average about 105). The styles are moderately uneven, somewhat long in length (about 0.7 to about 0.9 cm.), thin in caliper and loosely separated. Stigma color is between 8B and 10A. Style color is between 150B and 151D often lightly suffused with between 53B and 53C. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 6.7 to about 13.1 cm. in length and about 5.7 to about 9.5 cm. in width at the widest point, moderately crisp to somewhat leathery in texture, and glossy in finish on the upper side and matte in finish on the underside. The terminal leaflets are about 3.6 to about 5.5 cm. in length and about 2.2 to about 4.1 cm. in width at the widest point, shaped moderately ovate to somewhat oval with acuminate to somewhat acute apices and rounded to somewhat acute bases. Their margins are usually simply serrate. The venation pattern type is pinnate. The venation coloration of the upper surface is similar to the upper surface color of the mature leaf. The venation coloration of the lower surface is similar to the lower surface color of the mature leaf.

The upper surface color of the mature leaf is between 139A and 137A. The under surface color of the mature leaf is between 147B and 148C. The upper surface color of the young leaf is between 137C and 146A, often heavily suffused with between 187B and 183A. The under surface color of the young leaf is between 146B and 148D, often heavily suffused with between 187B and 183A.

The rachis is somewhat light to average in caliper and moderately rough. The upper side is shallowly grooved with few stipitate glands on the edges of the grooves. The under side of the rachis is moderately rough with very few stipitate glands and few small prickles. The rachis color is near 146D on the underside and near 146A on the upper side often moderately suffused on the young leaf with between 187B and 183A.

The stipules are about 0.9 to about 1.8 cm. in length and moderately narrow in width (about 0.3 to about 0.5 cm.) with moderately short straight points that usually turn out at an angle of more than 45 degrees. The under and upper surface color of the stipule is between 137A and 137B.

The petiole is somewhat light to average in caliper and moderately rough. The upper side is shallowly grooved with few stipitate glands on the edges of the grooves. The under side of the petiole is moderately rough with very few stipitate glands and few small prickles. The petiole is about 0.6 to about 1.7 cm. in length and about 0.1 to about 0.15 cm in width at the widest point. The petiole color is near 146D on the underside and near 146A on the upper side.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy upright medium height growing habit (about 120 to about 160 cm. in height and about 75 to about 90 cm. spread at the widest point), with full branching. It displays moderately vigorous growth and the canes are of medium caliper for the class (about 1.4 to about 2.2 cm. in diameter at the widest point).

The color of the major stems is between 146A and 146B. They bear some large prickles that are about 0.8 to about 1.0 cm. in length. The large prickles are almost straight to angled slightly downward with a short broad to oval base; prickle color is between 165C and 199B often moderately suffused with near 198B. The major stem bears few small prickles of similar shape and coloration.

The color of the branches is between 146B and 147B. They bear some large prickles which are of similar size and shape to the large prickles on the major stems; prickle color is between 160A and 151A. The branches bear no small prickles.

The color of the new shoots is between 146B and 147B often moderately suffused with between 183A and 187B. They bear some large prickles which are of similar size and shape to the large prickles on the major stems; prickle color is between 145A and 146D sometimes lightly suffused with near 187C. The shoots bear no small prickles.

I claim:

1. A new and distinct Floribunda rose plant of the variety substantially as described and illustrated herein.

* * * * *

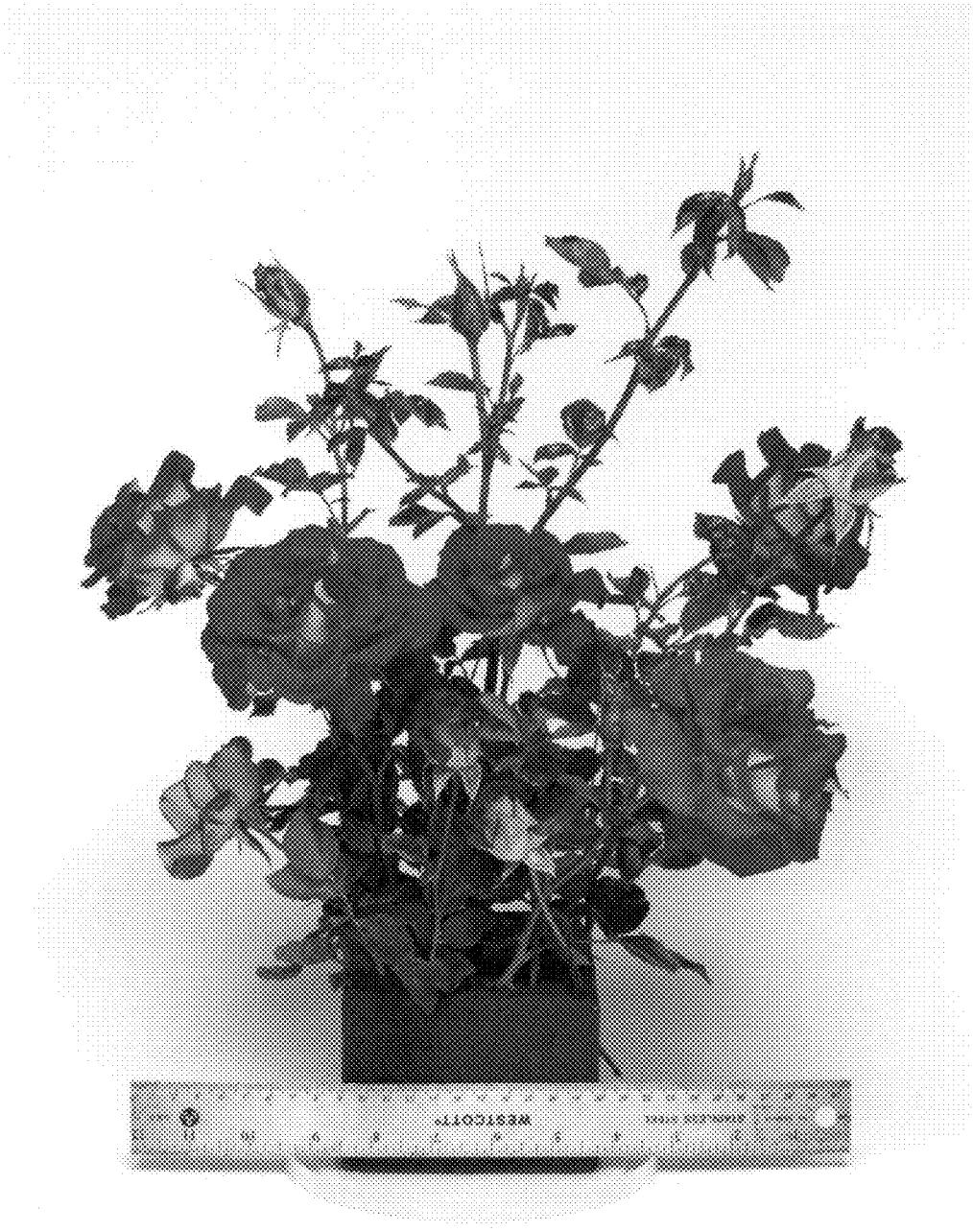
WESTCOTT